US006887417B1

(12) United States Patent
Gawreluk et al.

(10) Patent No.: US 6,887,417 B1
(45) Date of Patent: May 3, 2005

(54) CATHETER SLEEVE ASSEMBLY AND ONE STEP INJECTION MOLDING PROCESS FOR MAKING THE SAME

(75) Inventors: Craig N. Gawreluk, Park City, UT (US); Cynthia A. Castro, Sandy, UT (US); Weston F. Harding, Lehi, UT (US); Steven W. Johnson, West Jordan, UT (US); Wayne M. Parris, Draper, UT (US); Lantao Guo, Draper, UT (US); Michael C. Larsen, Sandy, UT (US)

(73) Assignee: BectonDickinson and Company, Franklin Lakes, NJ (US)

( * ) Notice: Subject to any disclaimer, the term of this patent is extended or adjusted under 35 U.S.C. 154(b) by 56 days.

(21) Appl. No.: 10/011,608

(22) Filed: Nov. 5, 2001

(51) Int. Cl.[7] .............................................. B29C 45/36
(52) U.S. Cl. ............................... 264/328.1; 264/328.12
(58) Field of Search ......................... 264/328.1, 328.12; 604/280

(56) References Cited

U.S. PATENT DOCUMENTS

| 2,330,399 A | | 9/1943 | Winder ........................ 128/249 |
| 3,385,553 A | | 5/1968 | Braun ......................... 249/142 |
| 3,727,613 A | | 4/1973 | Sorenson et al. ........ 128/214.4 |
| 3,901,965 A | | 8/1975 | Honeyman, III ............. 264/328 |
| 3,983,203 A | | 9/1976 | Corbett ........................ 264/150 |
| 4,126,291 A | * | 11/1978 | Gilbert et al. ................. 249/63 |

(Continued)

FOREIGN PATENT DOCUMENTS

| EP | 0761250 | 3/1997 |
| EP | 0 761 250 A1 | 3/1997 |
| EP | 1 116 567 A2 | 7/2001 |
| WO | WO 92/08598 | 5/1992 |

OTHER PUBLICATIONS

Shaosheng, Wang Qingmin, Wei Yuezhen, Zhang Zhiqian. "Relations of Weight–Average Molecular Weights and the Thermal Properties of N–Cyclohexyl Maleimide–Methyl Methacrylate". Journal of Applied Polymer Science, vol. 70, pp. 2001–2002 (1998).*

International Search Report (UPCT/US02/35380).

*Primary Examiner*—Michael P. Colaianni
*Assistant Examiner*—Monica A. Fontaine
(74) *Attorney, Agent, or Firm*—Madson & Metcalf

(57) ABSTRACT

An enhanced catheter introducer and method for making the same are disclosed. The catheter introducer may have a splittable sleeve assembly configured to be inserted into a blood vessel with a cannula. The cannula may then be removed, and a catheter may be inserted into the sleeve assembly. The sleeve assembly may be removed from the catheter by pulling handles of the sleeve assembly in different directions to split the sleeve assembly into two pieces. The sleeve assembly may have failure zones that enable the sleeve assembly to be easily split; the failure zones may take the form of thinned regions running along the length of the sleeve assembly. The sleeve assembly may be injection molded with a single step by injecting flows of molten plastic into a cavity of a mold such that the flows converge into an even distribution about the circumference of the sleeve. The mold may have a core pin designed to fit into the cavity. Through the use of the even distribution of flows, the core pin may seat within the cavity in an untensioned manner.

37 Claims, 5 Drawing Sheets

U.S. PATENT DOCUMENTS

| | | | | |
|---|---|---|---|---|
| 4,166,469 A | | 9/1979 | Littleford | |
| 4,243,050 A | | 1/1981 | Littleford | |
| 4,284,459 A | | 8/1981 | Patel et al. | 156/245 |
| 4,306,562 A | | 12/1981 | Osborne | |
| 4,360,024 A | | 11/1982 | Wallace | 604/256 |
| RE31,855 E | | 3/1985 | Osborne | |
| 4,743,420 A | * | 5/1988 | Dutt | 264/102 |
| 4,750,877 A | | 6/1988 | Mc Farlane | 425/573 |
| 4,877,394 A | | 10/1989 | Mc Farlane | 425/567 |
| 4,956,143 A | | 9/1990 | Mc Farlane | 264/334 |
| 5,167,634 A | * | 12/1992 | Corrigan et al. | 604/160 |
| 5,221,263 A | | 6/1993 | Sinko et al. | 604/161 |
| 5,318,542 A | * | 6/1994 | Hirsch et al. | 604/161 |
| 5,411,477 A | | 5/1995 | Saab | 604/96 |
| 5,510,065 A | | 4/1996 | Mc Farlane | 264/40.5 |
| 5,620,639 A | | 4/1997 | Stevens et al. | 264/85 |
| 5,735,819 A | | 4/1998 | Elliott | 604/161 |
| 5,743,882 A | | 4/1998 | Luther | 604/168 |
| 6,027,480 A | | 2/2000 | Davis et al. | 604/164 |
| 6,077,470 A | | 6/2000 | Beaumont | 264/297.2 |
| 6,120,483 A | | 9/2000 | Davey et al. | 604/247 |
| 6,192,568 B1 | | 2/2001 | Kafrawy et al. | 29/412 |
| 6,630,086 B1 | | 10/2003 | Goral et al. | |

* cited by examiner

US 6,887,417 B1

CATHETER SLEEVE ASSEMBLY AND ONE STEP INJECTION MOLDING PROCESS FOR MAKING THE SAME

BACKGROUND OF THE INVENTION

1. Field of the Invention

The present invention relates to medical systems and devices. More specifically, the present invention relates to catheter introducers with plastic sleeve assemblies, and to methods of injection molding sleeve assemblies with a single step.

2. Description of Related Art

There has been a longstanding need in the medical profession for devices and methods by which fluids can be injected into the body or "aspirated," or removed from the body. Due to the emergence of advanced catheter-related technologies, a larger number of medical procedures that have historically required surgery can now be performed intravenously. Procedures such as angioplasty and exploratory surgery can be carried out without making any incisions other than the puncture necessary to access a blood vessel and insert a catheter. Thus, there is a renewed need for safe, reliable, and comfortable methods of inserting and maintaining a catheter within a blood vessel.

A "catheter introducer" is a device that can be used to access a blood vessel for insertion of a catheter. A catheter introducer typically includes a "cannula," or needle that is used to puncture the patient's flesh and form an opening in the wall of the blood vessel. The cannula may have a hollow bore through which blood or other fluids can flow. A catheter introducer may also include a plastic sleeve assembly designed to fit around the cannula. A sleeve assembly may be used to maintain the opening in the wall of a blood vessel while the cannula is withdrawn. A catheter can then be inserted into the blood vessel through the sleeve assembly. Once the catheter has been inserted, the sleeve assembly can be removed from the blood vessel, along the catheter.

Although the use of the catheter introducer provides some improvements in the catheter insertion process, several problems remain. Many sleeve assemblies have tips that lack the precision to maintain a close fit over the cannula; hence, they irritate the walls of the blood vessel upon insertion into the vessel with the cannula. Some sleeve assemblies have a bent sleeve or a non-uniform wall thickness, and are therefore subject to puncture by the cannula or to leakage through a thin-walled portion the sleeve.

Furthermore, many sleeve assemblies cannot be easily removed from the catheter after they are withdrawn from the blood vessel. Such sleeve assemblies may present an obstruction during operation of the catheter. Indeed, an attempt to remove a sleeve assembly through the use of scissors or the like can cause damage to the catheter.

Some sleeve assemblies are made to split in half for removal from the catheter. Such sleeve assemblies are subject to a number of different problems, including premature splitting (i.e., splitting during assembly with the cannula or during insertion into the blood vessel), breakout (incomplete splitting), leakage through tear seams, and the like.

Additionally, sleeve assemblies are generally somewhat expensive to produce with traditional methods because several manufacturing steps are involved. A tubular sleeve is commonly produced through the use of an extrusion process. The sleeve may be attached to a molded handle/hub piece through the use of swaging or a similar process. The end of the sleeve is then processed in a tipping operation to create a tapered tip of the desired size and shape. The use of such a large number of processes makes the manufacture of sleeve assemblies unduly expensive and time-consuming.

Accordingly, a need exists for an improved sleeve assembly and manufacturing method for a catheter introducer. Such a sleeve assembly should preferably be easy to assemble with the cannula, and should cause a minimum of patient discomfort upon insertion into the blood vessel with the cannula. Additionally, the sleeve assembly should be easily removable from the catheter after withdrawal of the sleeve assembly from the blood vessel. Furthermore, such a sleeve assembly should be inexpensive and easy to produce, preferably with a minimum of manufacturing steps.

SUMMARY OF THE INVENTION

The apparatus of the present invention has been developed in response to the present state of the art, and in particular, in response to the problems and needs in the art that have not yet been fully solved by currently available catheter introducer sleeve assemblies and sleeve assembly manufacturing methods. Thus, it is an overall objective of the present invention to provide a sleeve assembly and method of manufacture by which inexpensive, comfortable, and safe catheter insertion can be performed.

To achieve the foregoing objective, and in accordance with the invention as embodied and broadly described herein in the preferred embodiment, a one-piece splittable sleeve assembly is provided, together with a method of injection molding the same with a single step. According to one configuration, the sleeve assembly may be used with a cannula assembly to form a catheter introducer. The cannula assembly may have a cannula held by a casing; the casing may have grips so that a person can apply manual pressure against the casing to press the cannula into the blood vessel.

The sleeve assembly may have a sleeve with a long, tubular shape, a hub with a somewhat wider tubular shape, a first handle extending from the hub, and a second handle extending from the hub, opposite the first handle. A first failure zone and a second failure zone may extend along the length of the sleeve and the hub. The first and second failure zones may be disposed on opposite sides of the sleeve and hub so that the sleeve is divided into two semi-tubular portions. A user can then pull the handles apart to separate the sleeve assembly along the failure zones, into two substantially equal parts. The two halves of the sleeve assembly can then be freely removed from the catheter.

In one embodiment, each failure zone comprises a thinned region. The thinned regions may simply be elongated indentations, in which the wall thickness is thinner than the surrounding material. The thinned regions may be formed on the outside of the sleeve, or on the inside where they cannot normally be seen by a user.

In the alternative, the failure zones need not have a thinner wall thickness than the surrounding regions. Rather, failure zones may be weakened in other ways. For example, the material of the failure zones may be comparatively weak due to positioning on a weld line of the sleeve, at which separate molten flow fronts meet during the molding process. Weld lines are weak because the leading edge of each converging flow front has a comparatively low temperature. As a result, the leading edges are in a less flowable state, and the flow fronts do not readily adhere to each other. Failure zones may also be provided by other changes in material properties, such as changes in molecular alignment or homogeneity.

The present invention also provides a method and related apparatus by which such a sleeve assembly may be inexpensively manufactured through the use of a single injection molding process. In one embodiment, a mold used for the injection molding process has a B-side and an A-side coupled to a nozzle of a plastic injection system. The A-side may have a floating plate and a top clamp plate. The B-side may have a cavity plate, a support plate, a bottom clamp plate, an ejector retainer plate, and an ejector backing plate.

The floating plate and the cavity plate may be configured to mate to produce a cavity into which plastic can be injected to form the sleeve assembly. The cavity may be sealed in plastic-tight fashion such that gas can escape the cavity during injection, but plastic is unable to escape. A core pin may protrude into the cavity from the floating plate, such that the cavity has a generally annular shape. The cavity may have a sleeve portion in which the sleeve is formed, a hub portion in which the hub is formed, and handle portions in which the handles are formed. The core pin may cooperate with the sleeve portion to form a sleeve annulus within the cavity. The sleeve portion may include a tip portion shaped to form the tip.

First and second ridges may protrude into the cavity from the sleeve portion to form the first and second thinned regions, respectively. In the alternative, ridges may be positioned on the core pin to form thinned regions on the interior diameter of the sleeve assembly. As another alternative, no ridges need be formed; the flows of molten plastic may simply be directed to form regions of comparatively low transverse tensile strength, such as weld lines.

The cavity plate may have a pair of split inserts that provide the shape of the sleeve portion of the cavity. The split inserts may face each other to form the sleeve portion; one of the ridges may be disposed on each of the split inserts. The cavity plate may also have a pilot bushing into which the core pin seats with a very small amount of clearance, so that air can escape around the pilot bushing while molten plastic is trapped. A vacuum fitting may draw air around the pilot bushing and out of the cavity.

The mold may form the sleeve with a high degree of molecular alignment along the length of the sleeve by providing a comparatively even flow of molten plastic around the circumference of the sleeve annulus. Such an even flow may be provided by providing a plurality of flows that converge and flow into the sleeve annulus substantially simultaneously.

For example, the floating plate may have a pair of substantially symmetrical flow paths through which molten plastic is able to travel from the nozzle to the handle portions of the cavity. Each handle portion may have a pin gate through which molten plastic emerges from the flow paths to enter the handle portions. The molten plastic may travel through the handle portions toward the hub in a substantially uniform manner. The molten plastic may then enter the hub in a substantially even distribution about a circumference of the hub. From the hub, the plastic may enter the sleeve annulus and move through the sleeve annulus, into the tip portion, while maintaining an even distribution about the circumference.

Thus, the two flows of molten plastic may reach the end of the tip portion to contact the pilot bushing simultaneously. Since molecules of molten plastic tend to align themselves with the direction in which the plastic flows, the result is a high degree of molecular alignment along the length of the sleeve, including the tip. The strength of the molded plastic part is greatest in the direction with which the molecules are aligned. Thus, the sleeve of the sleeve assembly has a comparatively high resistance to axial tension and compression, and a comparatively low resistance to lateral or transverse forces, such as the tension that will be applied to split the sleeve to remove the sleeve assembly from a catheter.

Additionally, the use of even flows of molten plastic makes it unnecessary to employ extra steps to protect the core pin against bending. Some traditional injection molding processes utilize an external mechanism, such as a hydraulically operated clamp, to tension a core pin or other protrusion to form a bore in the injection molded part. Such mechanisms add to the complexity of the molding apparatus and increase the cycle time of the injection molding process, thereby increasing the cost of the injection molded parts.

The plastic used in the injection molding process may also be carefully selected to provide certain characteristics that have been found to contribute to even flow and molecular alignment. For example, the plastic may have a melt flow high enough to fill the cavity at reasonable injection pressures, yet low enough to avoid excessive "flash," or extension through seams of the mold. A melt flow ranging from about 14 to 100 may be appropriate. Similarly, the selected plastic may have a critical shear rate high enough to maintain axial, or longitudinal molecular alignment, thereby keeping axial strength high while permitting splitting perpendicular to the longitudinal axis of the sleeve. According to one embodiment, the plastic of the sleeve assembly comprises at least 80% polypropylene, with up to 20% polyethylene.

After the plastic has been injected into the cavity, the mold may withdraw the core pin from the cavity while the sleeve assembly is still resting against the walls of the cavity. This may be accomplished by separating the top clamp plate, to which the core pin is attached, from the floating plate. The core pin is withdrawn through a hole in the floating plate. The B-side may then be moved away from the A-side to expose the cavity. The sleeve assembly may be ejected from the cavity by ejector pins attached to the ejector backing plate.

The resulting sleeve assembly may have accurate tip geometry that promotes easier and more comfortable insertion of the catheter introducer into the blood vessel. Furthermore, the sleeve assembly may split reliably and easily, with a minimal likelihood of premature splitting or breakout. The sleeve assembly may be rapidly and inexpensively manufactured by the injection molding process described above, without the need for separate attachment or tipping operations. Consequently, the catheter introducer and method of the present invention may contribute to the comfort, reliability, and cost effectiveness of medical care.

These and other objects, features, and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the apparatus, system, and method of the present invention, as represented in FIGS. 1 through 7, is not intended to limit the scope of the invention, as claimed, but is merely representative of presently preferred embodiments of the invention.

Long, thin, tubular members have traditionally been very difficult to injection mold for a number of reasons. One source of difficulty is the extremely high pressures involved in injection molding processes. Typically, to provide a rapid fill, the plastic is pressurized to several thousand pounds per square inch. Thus, when flows of plastic enter the cavity, any imbalance results in deflection of the pin. Even in multi-gated systems, in which multiple flows are used, flow imbalances often occur because the flows are not simultaneous, or are not evenly distributed about the pin.

Furthermore, even when the core pin is strongly tensioned, imbalanced flows may cause the resulting part to have a number of undesirable characteristics such as poor molecular orientation, excessive flash, internal stresses, or the like. Consequently, the part as a whole may perform inadequately.

As a result, many such thin tubular parts are produced with other processes, such as extrusion. The thin tubular parts are then attached to other parts through separate processes. For the reasons described above, such processing is disadvantageous.

The present invention utilizes a number of advances in part geometry, material selection, and mold configuration to enable one-step formation of a sleeve assembly for a catheter introducer. These advances will be shown and described in greater detail in connection with FIGS. 1 through 7, as follows.

Figure 1:
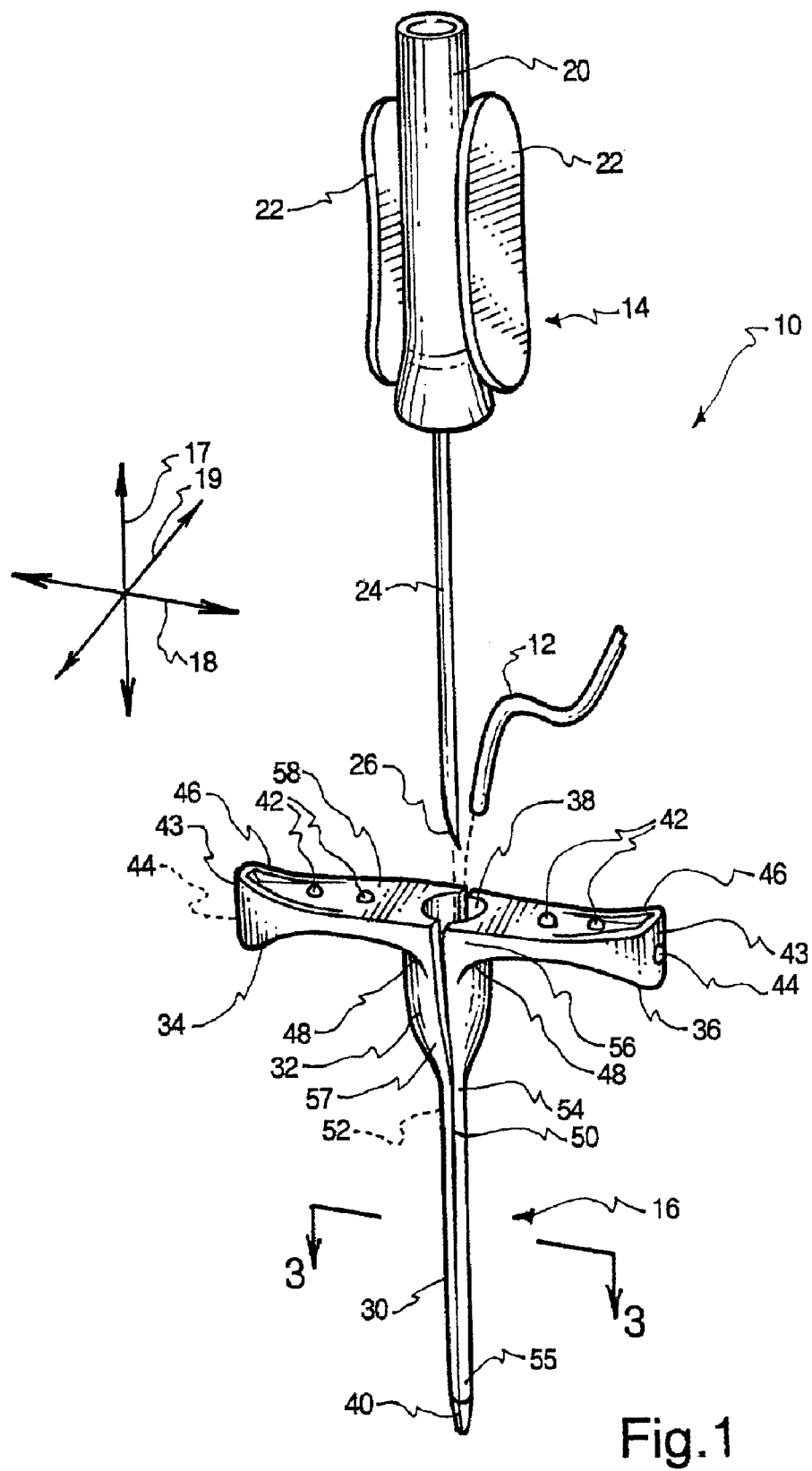
FIG. 1 is an exploded, perspective view of one embodiment of a catheter introducer according to the present invention, aligned with a catheter.

Referring to FIG. 1, a perspective view of one embodiment of a catheter introducer 10 is depicted. The catheter introducer 10 may be used to insert a catheter 12 safely into a patient's blood vessel with a minimum of discomfort. The catheter introducer 10 may have a cannula assembly 14 and a sleeve assembly 16. The catheter introducer 10 may also have a longitudinal direction 17, a lateral direction 18, and a transverse direction 19.

The cannula assembly 14 may have a casing 20 formed of a material such as plastic; a pair of grips 22 may extend laterally from the casing 20 to provide surfaces a user can grip, for example, with a thumb and forefinger, to safely hold the cannula assembly 14. The cannula assembly 14 may also have a cannula 24 with a hollow shape, through which fluid can pass into or out of the body. The cannula 24 may have a sharpened distal end 26.

The sleeve assembly 16 may have a sleeve 30 with a long, tubular shape sized to fit around the cannula 24. In this application, "tubular" does not require a mathematically perfect tube shape; rather, a tubular shape can be somewhat tapered, and can have irregularities such as notches, ridges, upward or downward steps in diameter, and the like. Preferably, the sleeve 30 is straight enough to fit over the cannula 24 without risk of puncturing the sleeve 30.

The sleeve assembly 16 may also have a hub 32 large enough that the hub 32 will not fit inside of an opening in the flesh made by the cannula 24. A first handle 34 may extend from the hub 32 in the lateral direction 18, and a second handle 36 may similarly extend from the hub 32 in the lateral direction 18, opposite the first handle 34. The hub 32 may have a luer taper 38 that provides an enlarged opening through which the cannula 24 can be easily inserted and guided into the sleeve 30. After insertion, the cannula 24 may be moved through the sleeve 30 until the sharpened distal end 26 of the cannula 24 protrudes from a tip 40 of the sleeve.

The first and second handles 34, 36 are preferably shaped to be gripped by a user. The handles 34, 36 may have a plurality of nubs 42 to ensure that a user is able to securely grip the handles 34, 36. The handles 34, 36 may also have outer edges 43, each of which has a gated region 44 through which molten plastic flowed to form the sleeve assembly 16. The gated regions 44 may simply appear as bumps left over from the process of stripping the sleeve assembly 16 from the mold; the operation of the gated regions and the mold will be described in greater detail subsequently.

The first and second handles 34, 36 may also have embankments 46 that protrude in the longitudinal direction 17 from the handles 34, 36 to make the handles 34, 36 easier to securely grip. The embankments 46 may merge relatively smoothly with the hub 32 via gussets 48. The gussets 48 may add rigidity to the attachment of the handles 34, 36 to the hub 32 to ensure that tension on the handles 34, 36 is transmitted to the sleeve 30 to induce splitting.

The sleeve 30 may also have a first failure zone 50 and a second failure zone 52 extending in the longitudinal direction 17, i.e., along the length of the sleeve 30, on opposite sides of the sleeve 30. The failure zones 50, 52 are elongated regions in which the sleeve 30 is somewhat weak against tensile forces acting on the sleeve 30 in the lateral direction 18. The first and second failure zones 50, 52 may extend along the hub 32 as well as the sleeve 30, so that tension applied on the handles 34, 36 can form a crack that propagates along the entire length of the sleeve assembly 16.

The failure zones 50, 52 may take a variety of configurations, as will be discussed in greater detail subsequently. For the sleeve assembly 16 of FIG. 1, the first and second failure zones 50, 52 comprise first and second thinned regions 50, 52. For this application, a "thinned region" is a region in which the wall thickness of a hollow member is smaller than that of surrounding regions. The geometry of the thinned regions 50, 52, as well as one manner in which the thinned regions 50, 52 may be formed, will also be shown and described in greater detail subsequently.

In this application, "proximal" and "distal" refer to positioning along the longitudinal direction 17. More specifically, "proximal" refers to features toward the top of FIG. 1, and "distal" refers to features toward the bottom of FIG. 1. The sleeve 30 may thus have a proximal end 54 and a distal end 55. The hub 32 may similarly have a proximal end 56 and a distal end 57. The hub 32 may also have a proximal abutment 58 against which the casing 20 of the cannula assembly 14 seats when the cannula 24 is fully inserted into the sleeve assembly 16. The proximal abutment 58 thus permits pressure in the longitudinal direction 17 to be transmitted from the casing 20 and grips 22 to the sleeve assembly 16, so that the sleeve assembly 16 is pressed into the opening in the blood vessel with the cannula 24.

The sleeve 30 may, if desired have a slight draft angle so that the sleeve 30 is slightly wider at the proximal end 54 than at the distal end 55. Thus, a slightly widening annular gap may exist between the cannula 24 and the sleeve 30 when the cannula 24 is positioned within the sleeve 30. Such a widening gap may be used to indicate proper insertion of the sharpened distal end 26 of the cannula 24 into the blood vessel by, for example, forming a notch (not shown) in the cannula 24 through which blood is able to flow from the cannula 24 into the annular gap between the cannula 24 and the sleeve 30. The sleeve 30 may be translucent so that a user can see the blood in the sleeve 30, or in an associated gap or conduit to ensure that proper insertion has occurred.

In the alternative, the sleeve 30 may have a draft angle of 0°, such that the sleeve 30 has no taper, except at the tip 40. The annular gap may then have a uniform cross sectional size along the length of the sleeve 30.

After the catheter introducer 10 has been inserted into a blood vessel, both the sharpened distal end 26 of the cannula 24 and a portion of the sleeve 30, including the tip 40, rest within the blood vessel. The cannula assembly 14 may then be withdrawn entirely from the sleeve assembly 16 so that only the sleeve 30 remains within the blood vessel. The catheter 12 may then be inserted into the luer taper 38 of the hub 32, and pushed through the sleeve 30 into the blood vessel. When the catheter 12 is in the blood vessel, the sleeve assembly 16 is no longer needed and may be removed to enhance the patient's comfort and to avoid obstructing operation of the catheter 12.

Figure 2:
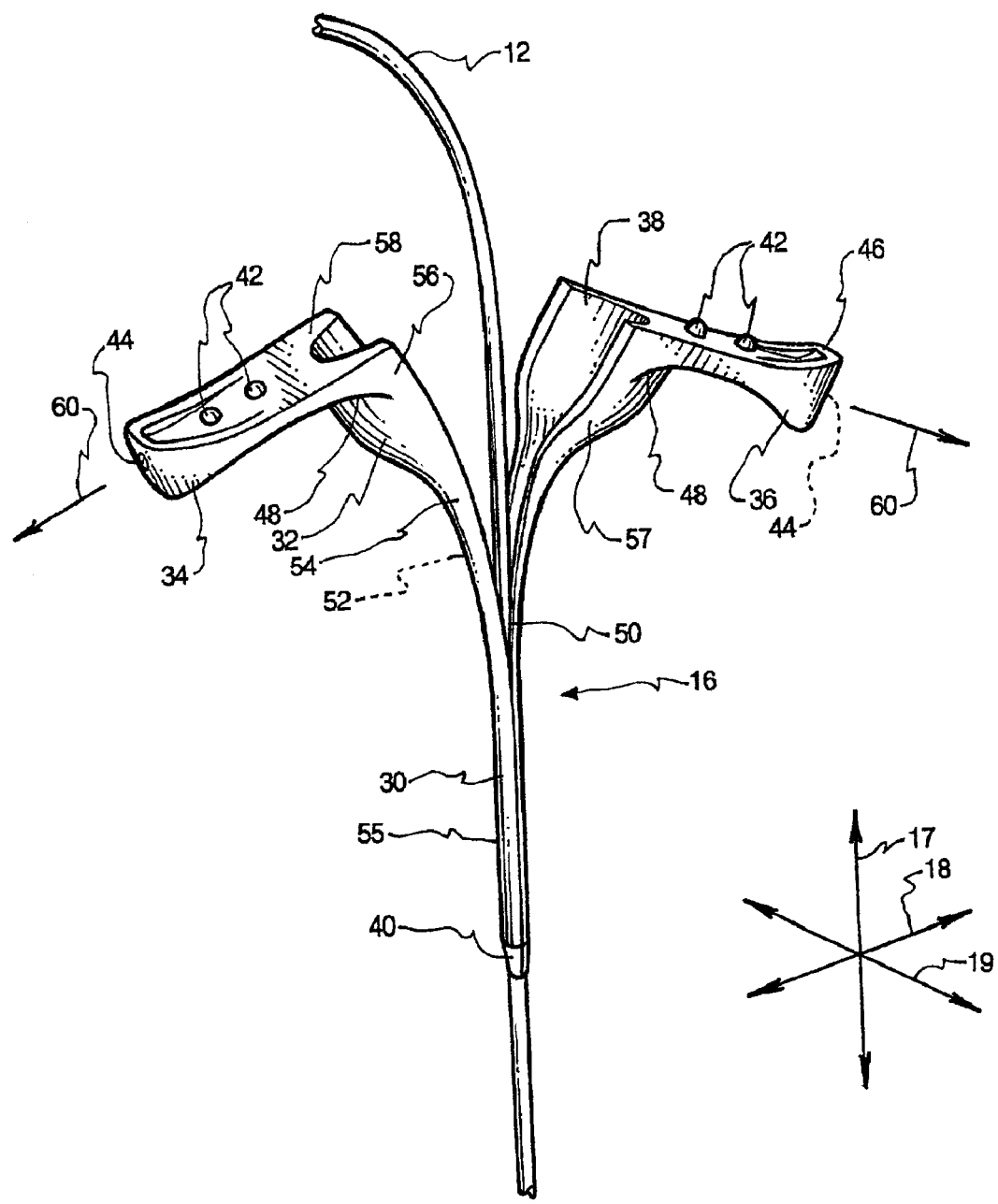
FIG. 2 is a perspective view of the sleeve assembly of FIG. 1 in a partially split configuration for removal from the catheter.

Referring to FIG. 2, one manner in which the sleeve assembly 16 may be removed from the catheter 12 is depicted. After the sleeve assembly 16 has been drawn out from the blood vessel along the catheter 12, opposing forces may simply be exerted on the handles 34, 36 along the arrows 60 shown in FIG. 2. When the handles 34, 36 are drawn apart, a crack propagates along the first and second thinned regions 50, 52, along the length of the sleeve assembly 16. Continued parting of the handles 34, 36 results in the fill separation of the two halves of the sleeve assembly 16. Once separated, the halves can then be removed from the catheter 12 and discarded.

Figure 3:
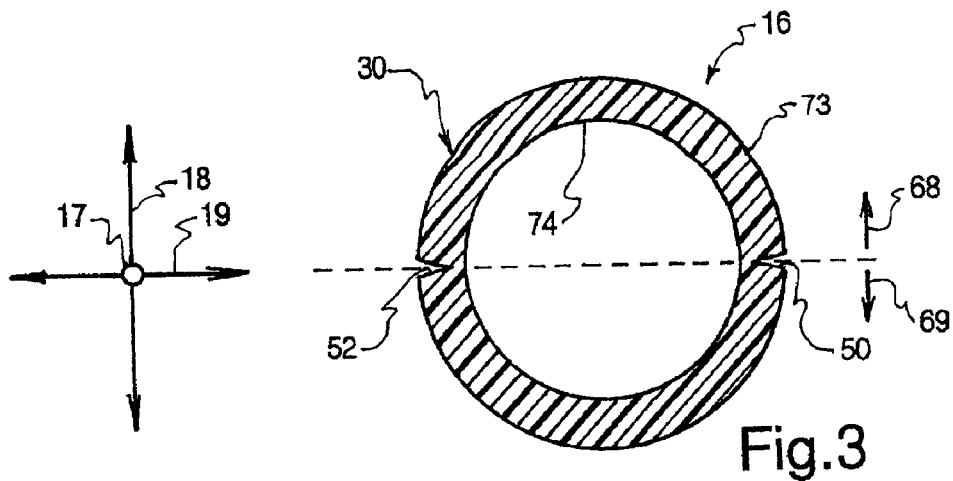
FIG. 3 is a top elevation, section view of the sleeve of the catheter introducer of FIG. 1.

Referring to FIG. 3, a cross sectional view of the sleeve assembly 16 is shown, taken through the sleeve 30. As shown, the first and second thinned regions 50, 52 take the form of notches in the material of the sleeve 30. The thinned regions 50, 52 may effectively separate the sleeve 30 into a first semi-tubular portion 68 and a second semi-tubular portion 69. "Semi-tubular" refers to a shape that is substantially half of a tube, split longitudinally. However, a "semi-tubular" shape need not be a precise half-tube, but may have features such as bevels that will be produced when the first and second thinned regions 50, 52 are split in half.

Furthermore, the thinned regions 50, 52 need not have a uniform wall thickness along the length of the sleeve assembly 16. For example, if it is desirable to decrease the "initiation force," or force required to commence splitting the sleeve assembly 16, the thinned regions 50, 52 may have a thinner wall thickness in the hub 32 than in the sleeve 30. The wall thickness of the thinned regions 50, 52 may thus be varied along the length of the thinned regions 50, 52 to obtain the desired force versus splitting characteristics of the sleeve assembly 30.

Additionally, to the extent that a lower initiation force, or force required to initiate splitting, is desired, two V-shaped notches (not shown) may optionally be formed between the first and second handles 34, 36, with the point of each "V" positioned at the end of one of the thinned regions 50, 52. The V-shaped notches may provide stress concentrations to initiate crack propagation along the thinned regions 50, 52, thereby decreasing the initiation force.

The sleeve 30 may also have an outside diameter 73 and an inside diameter 74. As shown, the first and second thinned regions 50, 52 are formed in the outside diameter 73. The thinned regions 50, 52 are shown with a generally V-shaped configuration; however, many other thinned region configurations may be used. For example, the thinned regions 50, 52 may, if desired, each have a somewhat broader, thin segment extending in the lateral direction 18, or may have a rounded notch shape. Those of skill in the art will recognize that many other configurations of the thinned regions 50, 52 may be used to provide failure zones.

Figure 4:
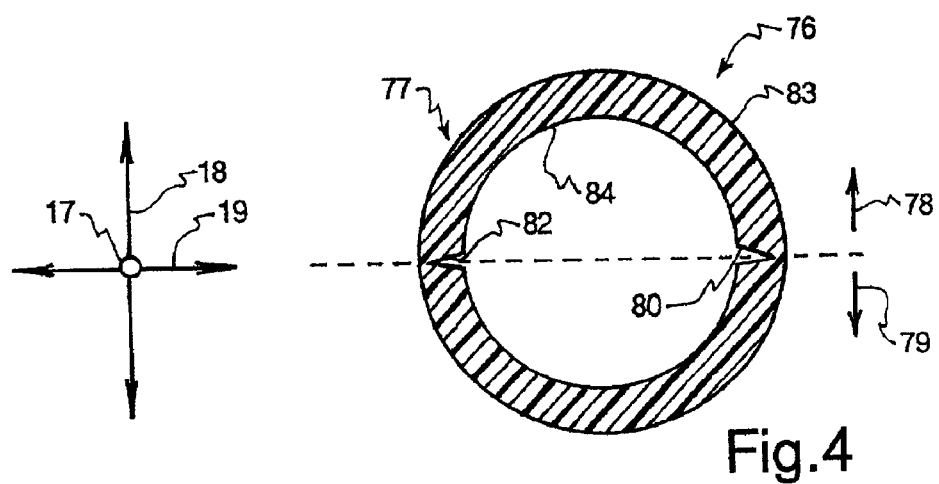
FIG. 4 is a top elevation, section view of a sleeve of an alternative embodiment of a catheter introducer according to the present invention.

Referring to FIG. 4, one such alternative configuration is shown. An alternative embodiment of a sleeve assembly 76 may have a sleeve 77 configured to split into a first semi-tubular portion 78 and a second semi-tubular portion 79. The sleeve 77 may have a first thinned region 80, a second thinned region 82, an outside diameter 83, and an inside diameter 84. In the embodiment of FIG. 4, the thinned regions 80, 82 are formed in the inside diameter 84. Thus, the thinned regions 80, 82 may not be easily visible to a user looking at the sleeve 77 of the sleeve assembly 76. Consequently, the sleeve assembly 76 may have a more robust appearance. If desired, failure zones on both the inside and outside diameters of a sleeve may be provided. For example, the thinned regions 50, 52 of FIG. 3 may be added to the sleeve 77 of FIG. 4 to further decrease the initiation force.

Figure 5:
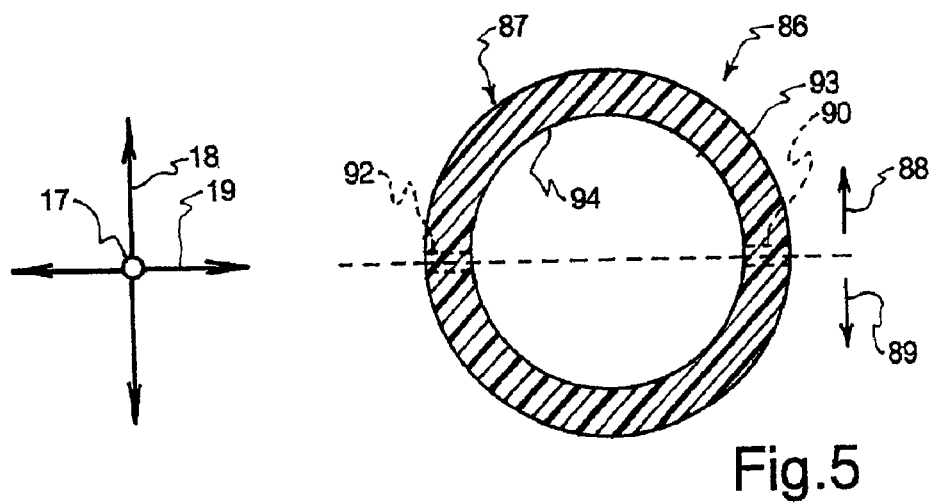
FIG. 5 is a top elevation, section view of a sleeve of another alternative embodiment of a catheter introducer according to the present invention.

Referring to FIG. 5, another alternative embodiment of a sleeve assembly 86 is shown. The sleeve assembly 86 may have a sleeve 87 configured to split into a first semi-tubular portion 88 and a second semi-tubular portion 89. In place of the thinned regions 50, 52 of FIG. 3 or the thinned regions 80, 82 of FIG. 4, the sleeve 87 may have a first weld line 90 and a second weld line 92. As shown, the weld lines 90, 92 may have a wall thickness substantially equal to that of the surrounding geometry.

The weld lines 90, 92 may simply be regions in which two or more flows of molten plastic have met during formation of the sleeve assembly 86. When two flows meet, even if they are generally flowing the same speed and direction, flow, pressure, and temperature differentials may tend to cause the molten plastic to move in an irregular manner along the interface between flows. Furthermore, the leading edges of the converging flow fronts will be comparatively cool, and therefore unable to properly mix and adhere to each other. Consequently, the weld lines 90, 92 are weaker than the surrounding material, even though they have the same nominal thickness. As with the sleeves 30 and 77, the sleeve 87 may have an outside diameter 93 and an inside diameter 94.

If desired, the weld lines 90, 92 may even be formed by injecting two separate flows of dissimilar resins into a single cavity. The use of dissimilar resins may further decrease the adhesion along the weld lines 90, 92, thereby further weakening the weld lines 90, 92. The dissimilar resins may include any two polymers or polymer blends that are chemically or compositionally different so that the adhesion force between the two materials is low enough to provide the desired splitting characteristics. The dissimilar materials may contain the same: components, but may contain them in varied proportions.

The dissimilar polymers may include a number of polymer family categories. For example, polyolefins such as high density polypropylene, low density polypropylene, and polypropylene may be used. Alternatively, vinyl polymers such as polyvinyl chloride, polystyrene, and polymethyl methacrylate may be used. As another alternative, polyamides such as polyether block amides may be used. As yet another alternative, polyesters such as polyethylene terephthalate, polybutylene terephthalate, polyethylene terephthalate glycol, polycarbonate, and polyurethane. Those of skill in the art will appreciate that other polymer families, other members of the polymer families listed above, copolymers of the polymer families listed above, and blends of the polymer families listed above may also be used to provide dissimilar resins for molding of the sleeve assembly 16.

Those of skill in the art will recognize that numerous other sleeve assemblies may be made within the scope of the present invention. The following discussion returns to the sleeve assembly 16 of FIGS. 1, 2, and 3 to describe one example of a method by which the sleeve assembly 16 may be injection molded.

Preferably, the sleeve assembly 16 is manufactured in a "one step" fashion. "One step" manufacturing refers to a process of completely forming an item in its final, usable condition, with a single manufacturing process. A manufacturing process such as injection molding may, itself, have several discreet steps; however, if no other operations such as core pin tensioning, "tipping" (insertion of the tip into a specialized tip mold), or part attachment need to be performed, the process is still a "one step" process.

Figure 6:
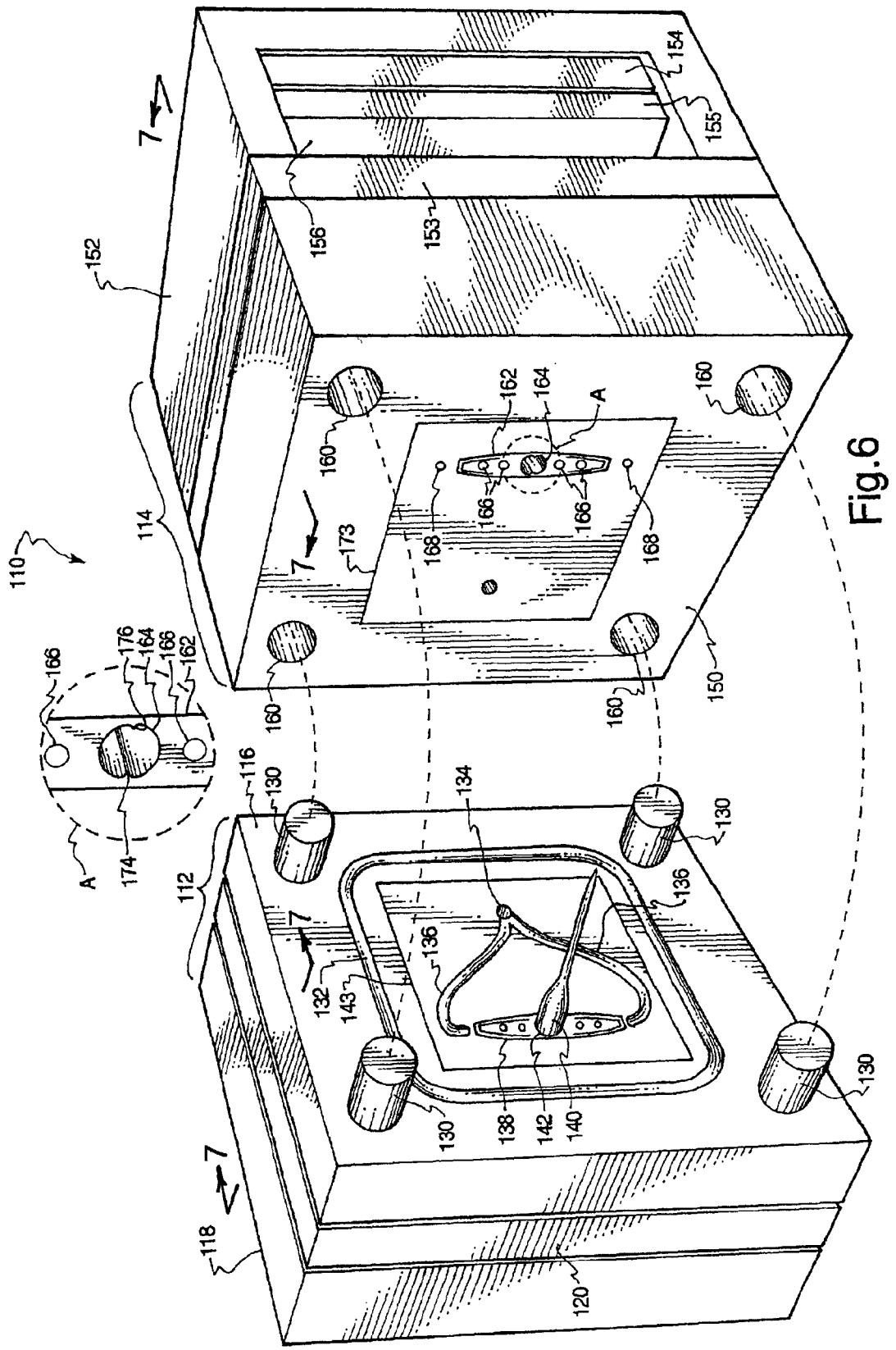
FIG. 6 is a perspective view of one embodiment of a mold suitable for producing the sleeve assembly of the catheter introducer of FIG. 1.

Referring to FIG. 6, one embodiment of a mold 110 capable of molding the sleeve assembly 16 in a one piece manner is shown. The mold 110 may be used with a wide variety of injection molding machines. Preferably, the injection molding machine used with the mold 110 is one capable of providing rapid and accurate acceleration and deceleration of the molten plastic into the mold 110 to ensure that the mold 110 is properly filled with each iteration. The injection molding machine, as well as other components that are typically used in an injection molding process, have been omitted from FIG. 6 to avoid obscuring aspects of the invention.

The mold 110 may have an A-side 112 that remains coupled to a nozzle of the injection molding machine, from which the mold 110 receives molten plastic. The mold 110 may also have a B-side 114 that translates with respect to the A-side 112 so that the A-side 112 and the B-side 114 can be selectively mated or disengaged.

The A-side 112 may have a floating plate 116 slidably mounted with respect to a top clamp plate 118 directly attached to the injection nozzle (not shown). The top clamp plate 118 may remain fixed in place, while the floating plate 116 is able to move a limited distance away from the top clamp plate 118. The motion of the floating plate 116 with respect to the top clamp plate 118 may be used to help remove the sleeve assembly 16 from the mold 110, in a manner that will be described in greater detail hereafter. A core pin retaining plate 120 may be positioned between the top clamp plate 118 and the floating plate 116, and may be affixed to the top clamp plate 118.

The floating plate 116 may have a plurality of leader pins 130 protruding from the floating plate 116, between the fixed and movable plate assemblies 112, 114. The leader pins 130 may, for example, be affixed to the top clamp plate 118, and may extend through holes in the core pin retaining plate 120 and the floating plate 116. Thus, the top clamp plate 118 and the floating plate 116 may slide relative to each other via the interaction of the leader pins 130 and the holes of the floating plate 116.

The floating plate 116 may also have a seal 132 that forms a bounded region within the leader pins 130. An sprue orifice 134 may be disposed within the bounded region of the seal 132; the sprue orifice 134 may be coupled via the top clamp plate 118 to the nozzle of the injection molding machine so that molten plastic travels from the nozzle to the sprue orifice 134, to emerge on the floating plate 116. The floating plate 116 may also have a pair of runner pathways 136 that convey molten plastic from the sprue orifice 134 toward a first cavity portion 138.

The runner pathways 136 may simply take the form of slots in the floating plate 116. Preferably, the runner pathways 136 are substantially symmetrical, so that they can convey simultaneous flows of molten plastic toward the first cavity portion 138 at substantially the same speed. Thus, the runner pathways 136 preferably open to the sprue orifice 134 with openings that are the same size; additionally, the runner pathways 136 preferably have the same length and cross sectional area.

The first cavity portion 138 may be shaped to form a proximal portion of the first and second handles 34, 36 as well as the proximal abutment 58 of the hub 32. A core pin 140 may extend from within the first cavity portion 138. The core pin 140 may be anchored to the top clamp plate 118 rather than the floating plate 116. The core pin 140 may thus extend from an opening 142 in the floating plate 116 as well as a hole (not shown) in the core pin retainer plate 120 such that the core pin 140 is positioned in the first cavity portion 138. Preferably, the opening 142 maintains a plastic-tight fit around the core pin 140 to ensure that plastic is unable to escape from the first cavity portion 138 via the opening 142. The core pin 140 and opening 142 may even provide an airtight fit, if desired; however, the core pin 140 is preferably able to slide relatively freely through the opening 142.

If desired, the sprue orifice 134, runner pathways 136, first cavity portion 138, and opening 142 may all be positioned on a modular block 143 affixed to the floating plate 116. The modular block 142 may permit rapid modification, repair, or replacement of various components of the floating plate 116, as well as the possibility of using the mold 110 to produce parts with different configurations.

The B-side 114 may have a cavity plate 150 configured to translate with respect to the floating plate 116 such that that the floating plate 116 and the cavity plate 150 can be selectively mated or disengaged. A bottom clamp plate 152 may be coupled to the cavity plate 150 such that the bottom clamp plate 152 translates with the cavity plate 150. A support plate 153 may be sandwiched between the cavity plate 150 and the bottom clamp plate 152. The B-side 114 may also have an ejector backing plate 154 and an ejector retainer plate 155 slidably positioned within a slot 156 between the cavity plate 150 and the bottom clamp plate 152. The ejector backing plate 154 and the ejector retainer plate 155 may help remove the sleeve assembly 16 from the mold 110 after the injection molding process is complete.

The cavity plate 150 may have a plurality of alignment holes 160 aligned with the leader pins 130 of the fixed plate to ensure that the floating plate 116 and the cavity plate 150 are able to mate precisely and reliably. A second cavity portion 162 of the cavity plate 150 may align with the first cavity portion 138 when the floating plate 116 and the cavity plate 150 mate to form a single cavity. A core pin aperture 164 may be disposed within the second cavity portion 162 to receive the core pin 140. The second cavity portion 162, together with the core pin aperture 164, may thus be shaped to form the remainder of the handles 34, 36, the hub 32, and the entire sleeve 30.

Ejector pins 166 may be substantially flush with the surface of the second cavity portion 162 when the ejector backing plate 154 is retracted, as shown in FIG. 6. Motion of the ejector backing plate 154 along the slot 156 may push the ejector pins 166 through the second cavity portion 162 to press the sleeve assembly 16 out of the mold. The configuration and operation of the ejector pins 166 will be shown and described in greater detail subsequently.

The cavity plate 150 may also have a pair of sub-gates 168 positioned on either side of the second cavity portion 162. The sub-gates 168 may receive the flows of molten plastic from the runner pathways 136 of the floating plate 116, and may conduct the flows into the gated regions 44 present in the handles 34, 36 of the sleeve assembly 16. Consequently, the plastic enters the first cavity portion 138 via the second cavity portion 162, despite the fact that the first cavity portion 138 is positioned on the floating plate 116 along with the runner pathways 1136. Like the floating plate 116, features of the cavity plate 150, such as the second cavity portion 162, the core pin aperture 164, and the sub-gates 168, may be positioned on a modular block 173 for rapid access, repair, or replacement.

The core pin aperture 164 may have structures that form the thinned regions 50, 52 during injection molding of the sleeve assembly 16. More specifically, referring to the expanded portion of FIG. 6, the core pin aperture 164 may have a first ridge 174 and a second ridge 176 disposed opposite the first ridge 174. The ridges 174, 176 may extend substantially along the length of the core pin aperture 164 to ensure that the thinned regions 50, 52 extend along the length of the sleeve assembly 16.

As mentioned previously, the thinned regions 50, 52 may each have a variable wall thickness along the length of the sleeve assembly 30. In order to provide such a variable wall thickness, each of the ridges 174, 176 may have a height that varies along the length of the core pin aperture 164. For example, if the thinned regions 50, 52 are to have a smaller wall thickness in the hub 32, the ridges 174, 176 may be made comparatively taller in the portion of the core pin aperture 164 in which the hub 32 is formed.

The ridges 174, 176 may reliably produce the thinned regions 50, 52 such that the problems present in known splittable introducer systems are reduced. In many such known introducer systems, splitting features are formed in a separate process from that used to create the sleeve assembly. Consequently, problems with the alignment and accuracy of the splitting features may arise. The ridges 174, 176 produce the thinned regions 50, 52 integrally with the remaining geometry of the sleeve 30. Accordingly, the thinned regions 50, 52 are consistently formed, and problems with premature splitting, excessive splitting resistance, and breakout may be virtually eliminated.

The ridges 174, 176 may be shaped to form V-shaped thinned regions 50, 52, as shown in FIG. 3. The ridges 174, 176 may also have a plurality of other configurations to form thinned regions with different shapes. In order to form the thinned regions 80, 82 on the inside diameter 84 of the sleeve assembly 76, for example, ridges may be positioned on the core pin 140. Of course, if weld lines are to be used for failure zones, no ridges need be included in the mold 110.

The first and second cavity portions 138, 162 and the core pin aperture 164, together, form a cavity into which the molten plastic flows in an even manner. The even flows act to provide a high degree of molecular alignment in the longitudinal direction 17 and to prevent deflection of the core pin 140. The manner in which molten plastic flows into the first and second cavity portions 138, 162 and the core pin aperture 164 will be shown and described in greater detail in connection with FIG. 7.

Figure 7:
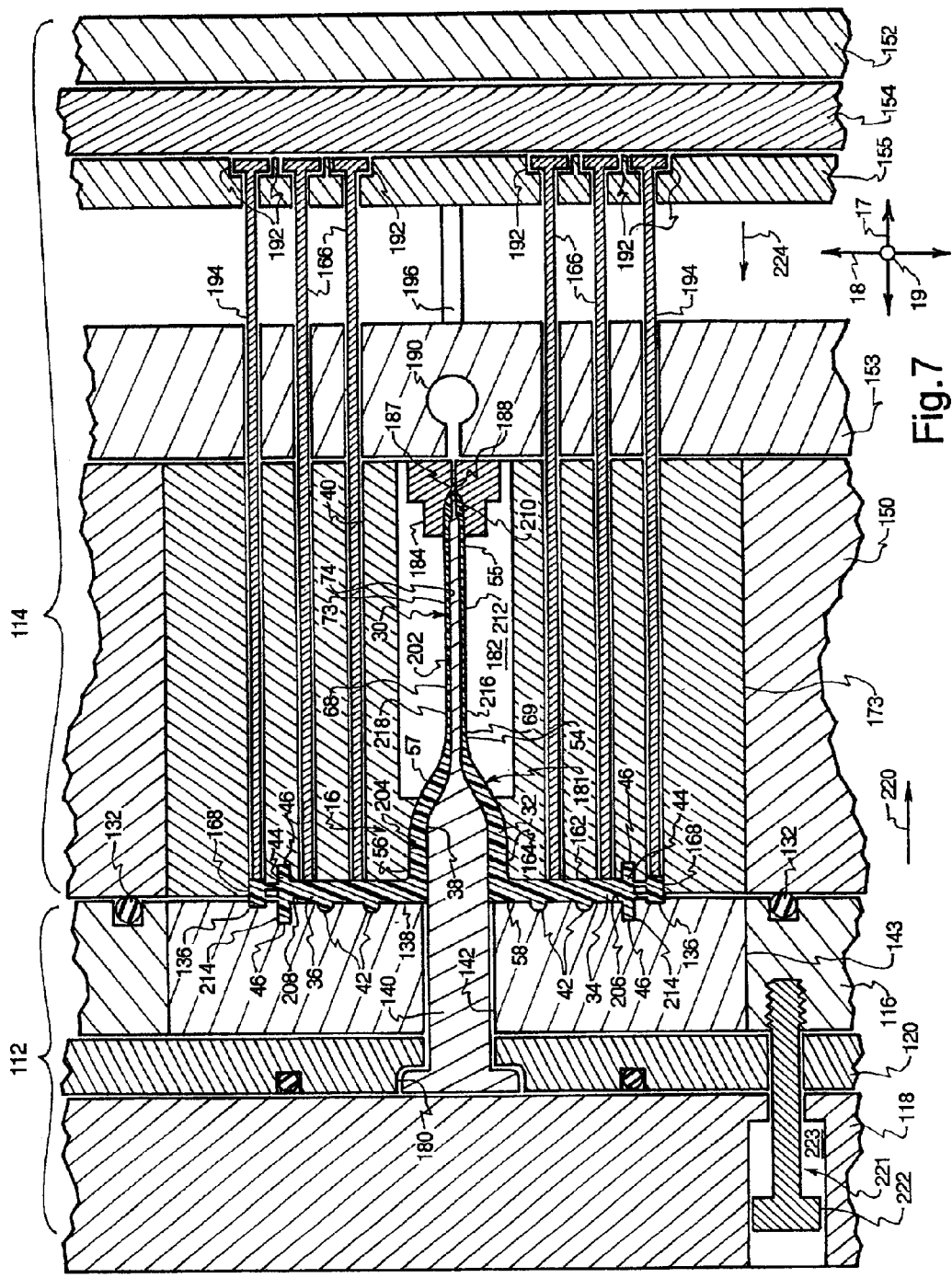
FIG. 7 is a side elevation, section view of the mold of FIG. 6, with floating plate and the cavity plate mated to provide a cavity for formation of the sleeve assembly, with a sleeve assembly resting in the cavity.

Referring to FIG. 7, a side elevation, section view of the mold 110 is shown, with the floating plate 116 and the cavity plate 150 mated for formation of the sleeve assembly 16. The sleeve assembly 16 is shown disposed in the cavity formed by the first and second cavity portions 138, 162 and the core pin aperture 164. The core pin 140 may be anchored to the top clamp plate 118, for example, by inserting the core pin 140 into a counterbore 180 of the core pin retainer plate 120 and attaching the core pin retainer plate 120 to the top clamp plate 118. As mentioned previously, the core pin 140 may then extend through the opening 142 to reach the cavity 181 formed by the first and second cavity portions 138, 162 and the core pin aperture 164.

The cavity plate 150 need not be solid, but may contain modular parts that provide the geometry of the cavity 181. For example, the cavity plate 150 may have a pair of split inserts 182 that have contouring to form the sleeve 30. Each of the split inserts 182 may be rectangular prismoidal in shape, with a tapered semi-cylindrical section removed to provide the geometry of the core pin aperture 164. The split inserts may be symmetrical, and may directly face each other in the transverse direction 19. Hence, only one of the split inserts 182 is visible in the cross sectional view of FIG. 7. The first and second ridges 174, 176 may be formed on the inward-facing surfaces of the split insert 182, and may also be formed in the cavity plate 150 adjacent to the split insert 182 so that the thinned regions 50, 52 will extend into the hub 30.

The cavity plate 150 may also have a pilot bushing 184, into which the core pin 140 extends when the floating plate 116 and the cavity plate 150 are mated, as shown in FIG. 7. The pilot bushing 184 and the split inserts 182 may be retained within the cavity plate 150 in a variety of ways, such as through the use of the support plate 153. The support plate 153 may simply be attached tightly to the cavity plate 150 to keep the pilot bushing 184 and the split inserts 182 in the proper position. In the alternative, a threaded retainer (not shown) or the like could be used to retain the pilot bushing 184.

The pilot bushing 184 may receive the distal end 187 of the core pin 140, and may support the distal end 187 against lateral motion. However, the pilot bushing 184 does not pull the core pin 140 in the longitudinal direction 17; thus, the core pin 140 is "substantially untensioned." Preferably, the pilot bushing and the distal end 187 are precision formed such that the distal end 187 fits within the pilot bushing 184 with only a very small clearance, such as a clearance on the order of two ten-thousandths of an inch (0.0002"). Thus, the distal end 187 is precisely fixed in place, and molten plastic is unable to escape from the cavity 181 between the distal end 187 and the pilot bushing 184.

The tip 40 of the sleeve assembly 16 may be formed within the pilot bushing 184. The tip 40 may have a tight clearance portion 188, in which the inside diameter 74 of the sleeve 30 is somewhat smaller. The tight clearance portion 188 may be sized to fit somewhat snugly over the cannula 24, so that the tip 40 of the sleeve assembly 16 is unable to move in the longitudinal, lateral, or transverse directions 17, 18, 19 during insertion of the sharpened tip 26 of the cannula 24 and the tip 40 of the sleeve assembly 16 into the blood vessel. Such a tight fit reduces patient discomfort and reduces the likelihood that the sleeve assembly 16 will split prematurely during insertion into the blood vessel. The tight clearance portion 188 may be formed by the distal end of the core pin 140, in which the diameter of the core pin 140 is reduced slightly.

In the alternative to complete formation of the tip 40 within the pilot bushing 184, the tip 40 may be created in roughened form in the injection molding process and further shaped through subsequent, or "secondary," processing. For example, the tip 40 may be injection molded with a tubular shape similar to that of the remainder of the sleeve 30. The tip 40 may then be tapered through reheating and shaping, mechanical cutting, or other similar operations. Although such operations require additional processing steps, the use of a sleeve assembly 16 with a one-piece, molded design may still serve to overcome many of the problems in the prior art, even if the tip 40 is not completely formed by the initial molding process.

The distal end 187 and the pilot bushing 184 may be made to fit together such that air is able to pass between the pilot bushing 184 and the distal end 187 to exit the cavity 181. If desired, a vacuum may be applied to the cavity 181 prior to injection of the molten plastic to evacuate air from the cavity 181, so that the molten plastic is able to entirely fill the cavity 181. The support plate 153 may, for example, have a vacuum channel 190 accessible from outside the mold 110. A vacuum fitting (not shown) may be attached to the support plate 153 and may be in gaseous communication with the pilot bushing 184 to draw air out of the cavity 181 through the pilot bushing 184. If desired, the pilot bushing 184 may even be made slightly porous to expedite the expulsion of air from the cavity 181. The vacuum fitting may be coupled to a vacuum source, such as a vacuum pump.

As shown, the ejector pins 166 that extend into the second cavity portion 162 may be attached to the ejector backing plate 154. Attachment may be accomplished by inserting the ejector pins 166 into counterbores 192 of the ejector retainer plate 155 and then attaching the ejector retainer plate 155 to the ejector backing plate 154. Additionally, ejector pins may be provided to eject the runners and the sprue from the mold 110. The runners are solidified plastic pieces formed in the runner pathways 136, and the sprue is a solidified plastic piece formed in the sprue orifice 134 of the floating plate 116. The runners and the sprue are ejected to avoid interference with the next injection cycle; they may be discarded or recycled for use in future injection cycles.

Consequently, the B-side 114 may have runner ejector pins 194 that extend into the sub-gates 168 of the cavity plate 150 to press the runners out of the opened mold 110. The geometry of the sub-gates 168 may serve to "strip," or remove, the runners from the gated regions 44 of the handles 34, 36. Additionally, the B-side 114 may have a sprue ejector pin 196 that ejects the sprue from the cavity plate 150. The sprue ejector pin 196 is not in line with the ejector pins 166 and the runner ejector pins 194, but is rather aligned with the sprue orifice 134. The runner ejector pins 194 and the sprue ejector pin 196 may also be retained within counterbores 192 of the ejector retainer plate 155.

The cavity 181, and more specifically, the core pin aperture 164, may have a sleeve portion 202 that forms the sleeve 30 of the sleeve assembly 16. As mentioned previously, the sleeve 30 may have a slight draft angle to provide a slightly tapered shape; such a draft angle may be present in both the outside diameter 73 and the inside diameter 74 of the sleeve 30. The draft angle may, for example, be on the order of 0.125°. In the alternative, the sleeve 30 may be molded with a draft angle of 0°. In any case, the sleeve portion 202 is shaped to produce the desired, draft angle.

A hub portion 204 of the cavity 181, or more specifically the core pin aperture 164, may form the hub 32, which may include a generally tubular portion and a conical portion to provide a transition to the smaller size of the sleeve 30. The cavity 181, or more specifically the first and second cavity portions 138, 162, may have a first handle portion 206 that forms the first handle 34 and a second handle portion 208 that forms the second handle 36. The sleeve portion 202 may include a tip portion 210 with a generally conical shape that forms the tip 40 of the sleeve 30. The interaction of the sleeve portion 202 and the core pin 140 may create a sleeve annulus 212, in which the sleeve 30 is formed. The sleeve annulus 212 need not be precisely annular, but may be tapered, or may have intruding geometry such as the ridges 174, 176 that form the thinned regions 50, 52.

The geometry of the cavity 181 may be specifically selected to ensure that the molten plastic is evenly distributed about the circumference of the core pin aperture 164 as the plastic flows through the sleeve annulus 212. Ideally, a tubular shape is formed with a "ring gate," or a gate in which molten plastic flows into the tubular cavity in a ring shaped configuration. The plastic is then evenly distributed about the circumference of the tubular shape as it enters the cavity.

Unfortunately, the existence of other geometry that is to be integrally formed with the tubular shape makes the use of a ring gate difficult or impossible. Furthermore, a ring gate adds to the difficulty of stripping the runners from the molded part because an entire ring of plastic attaches the runners to the molded part. Often, stripping must then be carried out manually or through the use of additional machinery.

The present invention provides an injection molding mold and method by which the even distribution of flows normally available only with a ring gate can be obtained with a plurality of pin gates or sub-gates, which are narrow gates that permit easy automatic stripping of the runners from the molded part. In the mold 110, the placement of the sub-gates 168 adjacent to the first and second handle portions 206, 208 has been selected to provide such an even distribution of flow, even though each gate channel 168 provides only one gate. A first flow (not shown) of molten plastic may enter the first handle portion 206 through the corresponding gate channel 168, and a second flow (not shown) may enter the second handle portion 208 through the other gate channel 168.

The handle portions 206, 208 may be shaped such that the cross section of each handle portion 206, 208 perpendicular to the lateral direction 18 remains substantially constant from the gate channel 168 to the hub portion 204. Thus, the first and second flows of molten plastic do not encounter any substantial flow restriction changes as they move toward the hub portion 204. The first and second flows produce a substantially uniform wall thickness in the handle portions 206, 208.

The embankments 46 of the handles 34, 36 may be formed by embankment portions 214 of the handle portions 206, 208. The embankment portions 214 provide additional flow area toward the outside edges of the handle portions 206, 208. Thus, although the first and second flows move relatively evenly along the first and second handle portions 206, 208, the additional molten plastic flowing through the embankments 46 may expedite flow into the regions of the hub portion 204 that are furthest from the handle portions 206, 208, i.e., the regions adjacent to the thinned regions 50, 52 within the hub portion 204.

The gussets 48 may similarly be formed by gusset portions (not visible in the cross section of FIG. 7), that also help to distribute the first and second flows around the circumference of the hub portion 204. The gusset portions may also provide a uniform cross sectional area for flows of molten plastic.

Consequently, although the first and second flows enter the cavity 181 from only two sides of the hub portion 204, the first and second flows may converge at the hub portion 204 in such a manner that the molten plastic is substantially evenly distributed about the circumference of the hub portion 204. The molten plastic then flows through the hub portion 204 substantially evenly, and passes into the sleeve annulus 212 in a substantially even distribution about the circumference of the sleeve annulus 212. Thus, the hub portion 204 acts somewhat like a ring gate, in that molten plastic flows ring-like from the hub portion 204 to the sleeve annulus 212.

Once in the sleeve annulus 212, the molten plastic may maintain a substantially even distribution about the core pin 140. The sleeve annulus 212 may be said to have a first semi-tubular portion 216 through which the first flow of molten plastic travels, and a second semi-tubular portion 218 through which the second flow of molten plastic travels.

Consequently, the core pin 140 is under substantially the same pressure from all sides, and no significant deflection of the core pin 140 occurs. The molten plastic may continue to flow evenly into the tip portion 210 until the tip portion 210 is filled. The injection molding machine may be configured to rapidly step down the pressure of the plastic within the mold 11d at a time selected to induce the molten plastic to stop flowing as soon as the tip portion 210 is filled.

Thus, the sleeve 30, including the tip 40, may maintain a comparatively evenly formed configuration with a high degree of longitudinal molecular alignment, or molecular alignment in the longitudinal direction 17. Longitudinal molecular alignment is desirable to prevent failure of the sleeve assembly 16 under the stresses of insertion.

The circumferential molecular alignment, or alignment in the lateral and transverse directions 18, 19, may be somewhat smaller than the longitudinal molecular alignment because the lateral and transverse directions 18, 19 are perpendicular to the direction in which molten plastic flows through the sleeve annulus 212 during the injection molding process. The resulting decreased strength in the lateral and transverse directions 18, 19 may be advantageous because the sleeve assembly 16 may be split with comparatively little resistance.

The plastic that is used to form the sleeve assembly 16 may be optimized to the pressure and temperature characteristics of the molding process as well as to the geometry of the cavity 181. For example, the plastic may have a melt flow high enough to ensure that the entire cavity 181 is filled within a reasonable cycle time, yet low enough to avoid excessive flash or circulation within the cavity 181 after filling. More specifically, the plastic may have a melt flow ranging from about 14 to about 100. Yet more specifically, the plastic may have a melt flow ranging from about 30 to about 50.

Additionally, it is desirable for the plastic used to have a critical shear rate high enough to avoid excessive molecular shear during the injection process. Other material properties such as the melting point, density, yield strength, ultimate strength, creep resistance, and fatigue resistance may also play a part in the selection of the plastic. The plastic may be a blend of multiple polymeric or non-polymeric materials.

According to one embodiment, the plastic includes polypropylene ranging from about 50% to about 100% by weight. The use of 100% polypropylene may provide excess tensile strength, thereby making the sleeve 30 difficult to split. The plastic may be about 80% polypropylene by weight, in which case the remainder of the plastic, i.e., up to about 20% by weight, may be polyethylene. Up to 100% polyethylene, by weight, may be used; however, the strength of the tip 40 may suffer as a result. Thus, when selecting the proportions of materials used to form the plastic, the strength of the tip 40 must be balanced against the ease of splitting the sleeve 30.

Additionally, the proportions of materials used to form the plastic may also be selected to provide a critical shear rate high enough that the molecules of the plastic are able to maintain a high degree of alignment during injection. The critical shear rate of polypropylene may also be enhanced by adding polyethylene.

The melt flows described above relate to tests commonly performed in connection with polypropylene. If the plastic includes other materials such as polyethylene, their melt flows should fall within a range similar to that described above when converted to the polypropylene scale. Furthermore, all of the materials used in the plastic should preferably have similar melt flows so that the materials do not separate upon injection into the cavity 181.

In certain implementations, the cavity 181 may be completely filled within about 0.2 seconds. For example, the cavity 181 may be filled in about 0.10 to about 0.15 seconds. After the cavity 181 has been filled, the molten plastic within the cavity 181 may be permitted to cool and solidify. Heat exchangers or the like, as known in the art, may be coupled to the mold 110 to facilitate cooling of the plastic within the cavity 181. Cooling may require a few seconds of time.

After the sleeve assembly 16 has solidified, the floating plate 116 may be moved away from the top clamp plate 118 in the direction shown by the arrow 220, thereby pulling the opening 142 along the core pin 140 to effectively retract the core pin 140 from the core pin aperture 164. During motion of the floating plate 116, the floating plate 116 and the cavity plate 150 may remain together so that the sleeve assembly 16 is still locked within the cavity 181. Thus, the core pin aperture 164 may provide support to for the relatively thin structure of the sleeve assembly 16 while the core pin 140 is withdrawn. The support provided by the core pin aperture 164 helps to prevent damage to the sleeve assembly 16, such as premature splitting and the like.

After the core pin 140 has been withdrawn, completely or in part, from the core pin aperture 164, the floating plate 116 and the cavity plate 150 may be disengaged by moving the B-side 114 away from the A-side 112 in the direction shown by the arrow 220 to open the cavity 181. Disengagement of the floating plate 116 from the cavity plate 150 is triggered by a shoulder bolt 221 with a head 222 that moves within a bore 223 of the top clamp plate 118. When the head 222 abuts the interior end of the bore 223, the floating plate 116 may be unable to move further from the top clamp plate 118.

A removable engagement device (not shown) such as a frictional clamp may be used to attach the floating plate 116 to the cavity plate 150 during injection. When the cavity plate 150 is pulled away from the floating plate 116 with a threshold force such as the force provided by the shoulder bolt 221, the engagement device disengages to permit separation of the floating plate 116 from the cavity plate 150.

The fully formed sleeve assembly 16, the runners, and the sprue may then be ejected through the use of the ejector pins 166, the runner ejector pins 194, and the sprue ejector pin 196. More specifically, the ejector backing plate 154 may be moved through the slot 156 in the direction shown by the arrow 224 to propel the ejector pins 166, the runner ejector pins 194, and the sprue ejector pin 196 toward the floating plate 116.

As mentioned previously, the geometry of the sub-gates 168 may shear the runners from the handles 34, 36 so that the sleeve assembly 16 is separated from the runners and the sprue. The sleeve assembly 16 may advantageously have a center of gravity toward the handles 34, 36 so that the sleeve assembly 16 drops from the mold 110 with the handles 34, 36 downward. Such an orientation may protect the sleeve 30 and the tip 40 from damage upon impact.

The sleeve assembly 16 of the present invention may provide several advantages over previously known catheter introduction systems. The sleeve assembly 16 may enhance comfort and convenience through easy assembly with the cannula assembly 14, comfortable insertion into the blood vessel, and reliable removal from the catheter 12. Such benefits are obtained, in part, via the enhanced straightness of the sleeve 30, the precision of the tip 40, and the reliable operation of the failure zones 50, 52.

Furthermore, the injection molding method presented herein enables the production of the sleeve assembly 30 with a high degree of reliability, rapidity, and cost effectiveness. Through the use of a uniform distribution of molten plastic, the longitudinal molecular alignment of the plastic can be maintained, and excessive flash can be avoided. All parts of the sleeve assembly 16 are produced substantially simultaneously with a single injection molding operation; thus, each sleeve assembly 16 can be produced rapidly reliably, and at low cost.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by united states Letters Patent is:

1. A method for injection molding a sleeve assembly for a catheter introducer, the method comprising:

providing a mold with a cavity dimensioned to produce a sleeve assembly for a catheter introducer, the cavity having a sleeve portion and a hub portion;

providing a core pin;

positioning the core pin within the cavity such that the core pin is supported at both ends in a substantially untensioned manner; and pressing molten plastic into the hub portion such that the molten plastic travels through a sleeve annulus between the sleeve portion and the substantially untensioned pin, wherein the molten plastic is substantially evenly distributed about a circumference of the sleeve annulus during motion through the annulus.

2. The method of claim 1, wherein pressing molten plastic into the hub portion comprises:

pressing a first flow of molten plastic into the hub portion; and pressing a second flow of molten plastic into the hub portion, opposite the first flow of molten plastic such that the first and second flows travel through the sleeve annulus substantially simultaneously.

3. The method of claim 2, wherein the cavity further comprises a first handle portion and a second handle portion, and wherein pressing molten plastic into the hub portion further comprises injecting the first and second flows through first and second gates formed in outer edges of the first and second handle portions of the cavity, respectively.

4. The method of claim 3, wherein the first and second handle portions are shaped to distribute the first and second flows substantially evenly about a circumference of the hub portion.

5. The method of claim 3, wherein providing the mold further comprises providing first and second gusset portions within the cavity to couple the first and second handle portions to the hub portion.

6. The method of claim 1, further comprising selecting a plastic from the group consisting of olefins, polyolefins, and combinations of olefins and polyolefins to substantially form the sleeve assembly for a catheter introducer.

7. The method of claim 6, wherein the plastic comprises at least about 50% polypropylene by weight.

8. The method of claim 7, wherein the plastic comprises at least about 80% polypropylene by weight.

9. The method of claim 8, wherein the plastic consists essentially of polypropylene and polyethylene.

10. The method of claim 1, wherein the sleeve portion comprises a tip portion with a tapered shape, and wherein pressing molten plastic into the hub such that the molten plastic travels through the sleeve annulus comprises inducing the molten plastic to move into the tip portion such that the molten plastic is substantially evenly distributed about the circumference upon entry into the tip portion.

11. The method of claim 10, wherein inducing the molten plastic to move into the tip portion comprises molding a tip with a tapered shape suitable for comfortable introduction into a blood vessel in conjunction with a cannula.

12. The method of claim 10, wherein inducing the molten plastic to move into the tip portion comprises molding a shape suitable for secondary processing to provide a tip suitable for introduction into a blood vessel in conjunction with a cannula.

13. The method of claim 10, wherein providing a core pin comprises providing a core pin with a tapered shape such that the sleeve assembly has a sleeve with a tapered inside diameter.

14. The method of claim 1, wherein the sleeve portion comprises a pair of ridges disposed on opposite sides of the sleeve portion, the ridges protruding into the cavity, and wherein pressing molten plastic into the hub such that the molten plastic travels through the sleeve annulus comprises forming thinned regions as the molten plastic solidifies around the ridges, the thinned regions serving as failure zones to permit splitting of the sleeve assembly.

15. The method of claim 1, wherein pressing molten plastic into the hub such that the molten plastic travels through the sleeve annulus comprises directing flows of the molten plastic to converge to form weld lines along a length of the sleeve portion, the weld lines serving as failure zones to permit splitting of the sleeve assembly.

16. The method of claim 1, wherein pressing the molten plastic into the hub such that the molten plastic travels through the sleeve annulus comprises directing flows of the molten plastic to form regions that have a degree and orientation of molecular alignment along a length of the sleeve portion such that the regions serve as failure zones to permit splitting of the sleeve assembly.

17. A method for injection molding a sleeve for a catheter introducer, the method comprising:
  providing a mold with a cavity dimensioned to produce a sleeve for a catheter introducer, the cavity having a sleeve annulus, the sleeve annulus having a first semi-tubular portion and a second semi-tubular portion;
  providing a core pin and positioning the core pin within the cavity such that it is supported at both ends in a substantially untensioned manner;
  pressing a first flow of molten plastic into the first semi-tubular portion such that the first flow is substantially evenly distributed about a circumference of the first semi-tubular portion during motion of the first flow through the first semi-tubular portion; and
  pressing a second flow of molten plastic into the second semi-tubular portion such that the second flow is substantially evenly distributed about a circumference of the second semi-tubular portion during motion of the second flow through the second semi-tubular portion.

18. The method of claim 17, wherein the sleeve annulus comprises a tip portion with a tapered shape, wherein the tip portion is overlapped by the first and second semi-tubular portions, the method further comprising conveying the first and second flows into the tip portion substantially simultaneously.

19. The method of claim 18, further comprising substantially stopping motion of the first and second flows when the first and second flows have penetrated the tip portion.

20. The method of claim 17, wherein the mold further comprises a first ridge oriented along a length of the sleeve annulus between the first and second semi-tubular portions, and a second ridge oriented along a length of the sleeve annulus between the first and second semi-tubular portions and opposite the first ridge, the first and second ridges operating to create first and second thinned regions in the sleeve upon solidification of the first and second flows of molten plastic.

21. The method of claim 17, wherein the cavity further comprises a first handle portion in fluid communication with the first semi-tubular portion and a second handle in fluid communication with the second semi-tubular portion, and wherein pressing a first flow of molten plastic into the first semi-tubular portion comprises pressing the first flow through a gate of the first handle portion, and wherein pressing a second flow of molten plastic into the second semi-tubular portion comprises pressing the second flow through a gate of the second handle portion.

22. A method for forming a sleeve for a catheter introducer, the method comprising:
  providing a mold comprising a cavity dimensioned to produce a sleeve for a catheter introducer, the cavity containing a sleeve annulus, the mold further comprising a first ridge oriented along a length of the sleeve annulus and disposed to protrude into the sleeve annulus, and a second ridge oriented along a length of the sleeve annulus and disposed to protrude into the sleeve annulus opposite the first ridge;
  providing a core pin and positioning the core pin within the cavity such that it is supported at both ends in a substantially untensioned manner:
  injecting molten plastic into the sleeve annulus; and
  permitting the molten plastic to cool into a sleeve with a first thinned region formed by the first ridge and a second thinned region formed by the second ridge.

23. The method of claim 22, wherein the cavity comprises a sleeve portion, wherein the core pin extends through the sleeve portion to form the sleeve annulus, and wherein the first and second ridges are disposed on the sleeve portion and protrude inward toward the pin.

24. The method of claim 22, wherein the cavity comprises a sleeve portion, wherein the core pin extends through the sleeve portion to form the sleeve annulus, and wherein the first and second ridges are disposed on the core pin and protrude outward toward the sleeve portion.

25. The method of claim 22, wherein the first and second ridges are shaped such that each of the first and second thinned regions has a variable wall thickness along the length of the sleeve annulus.

26. A method for forming a sleeve for a catheter introducer, the method comprising:
  providing a mold having a cavity dimensioned to produce a sleeve for a catheter introducer, the cavity comprising a sleeve annulus;
  providing a core pin to be positioned in the cavity, wherein the core pin is supported at both ends in a substantially untensioned manner;
  injecting molten plastic into the sleeve annulus such that the plastic has a longitudinal molecular alignment along a length of the sleeve annulus and a circumferential molecular alignment perpendicular to the length of the sleeve annulus, wherein the longitudinal molecular alignment is comparatively greater than the circumferential molecular alignment; and
  wherein injection of the molten plastic results in the creation of a first failure zone in the molten plastic, the first failure zone extending substantially along the length of the sleeve, and a second failure zone in the molten plastic, the second failure zone extending substantially along the length of the sleeve opposite the first failure zone.

27. The method of claim 26, wherein injecting molten plastic into the sleeve annulus comprises distributing the molten plastic substantially evenly about a circumference of the sleeve annulus such that the molten plastic flows substantially evenly along the length of the sleeve annulus.

28. The method of claim 26, wherein the first and second failure zones comprise regions with a degree and orientation of molecular alignment selected to enable splitting along a length of the sleeve.

29. A method for forming a sleeve assembly for a catheter introducer, the method comprising:
  providing a mold comprising a floating plate having a core pin extending therefrom and a cavity plate shaped to cooperate with the floating plate to form a cavity;
  mating the floating plate and the cavity plate such that the core pin extends into the cavity, wherein the core pin is supported at both ends in a substantially untensioned manner, wherein the cavity is sealed in a plastic-tight fashion;

injecting molten plastic into the cavity;

solidifying the molten plastic to form a sleeve assembly; and at least partially withdrawing the core pin through the floating plate while the floating plate and the cavity plate are mated to remove the core pin from the sleeve assembly.

30. The method of claim 29, further comprising ejecting the sleeve assembly from the cavity after motion of the core pin through the floating plate.

31. The method of claim 30, wherein at least partially withdrawing the core pin through the floating plate comprises sliding the floating plate away from a top clamp plate, wherein the core pin is attached to the top clamp plate and wherein the core pin extends through a hole in the floating plate.

32. The method of claim 31, wherein ejecting the sleeve assembly from the cavity comprises sliding an ejector backing plate toward the cavity plate, wherein the ejector backing plate has a plurality of ejector pins attached thereto to press the sleeve assembly out of the cavity.

33. The method of claim 29, wherein mating the floating plate and the cavity plate comprises translating the cavity plate into engagement with the floating plate.

34. A method for forming a tip for a sleeve of a catheter introducer, the method comprising:

providing a mold having a cavity, the cavity having a sleeve portion with a substantially annular shape, the sleeve portion having a tip portion with a tapered outside diameter;

positioning a core pin within the cavity to form a sleeve annulus between the sleeve portion and the pin, the core pin being supported at both ends in a substantially untensioned manner; and injecting molten plastic into the cavity such that the molten plastic travels through the sleeve annulus and into the tip portion, wherein, the molten plastic is substantially evenly distributed about a circumference of the sleeve annulus when the molten plastic enters the tip portion.

35. The method of claim 34, wherein injecting molten plastic into the cavity comprises:

injecting a first flow of molten plastic into a first semi-tubular portion of the sleeve portion, and injecting a second flow of molten plastic into a second semi-tubular portion of the sleeve portion, wherein the first and second flows travel through the sleeve portion to reach the tip portion substantially simultaneously.

36. The method of claim 34, wherein the mold further comprises a pilot bushing shaped to form the tip portion of the cavity, wherein positioning the core pin within the cavity comprises inserting a distal end of the core pin into the pilot bushing to provide support for the distal end of the pin.

37. The method of claim 34, further comprising substantially dropping pressure against the molten plastic to substantially arrest motion of the molten plastic when the tip portion has been filled.

* * * * *